United States Patent [19]

Bourinbaiar

[11] Patent Number: 5,552,382
[45] Date of Patent: Sep. 3, 1996

[54] GRAMICIDIN AS A SPERMICIDE AGAINST SEXUAL TRANSMISSION OF HIV

[75] Inventor: Aldar S. Bourinbaiar, New York, N.Y.

[73] Assignee: Metatron, Inc., Deer Park, N.Y.

[21] Appl. No.: 348,482

[22] Filed: Dec. 2, 1994

[51] Int. Cl.⁶ .................................................. A61K 38/00
[52] U.S. Cl. .................................................... 514/14
[58] Field of Search ...................................... 514/14

[56] References Cited

PUBLICATIONS

Cates et al.; "Family Planning Perspective", 24:75–84, 1992.
Merson, "Science", 260:1266–1268, 1993.
Bourinbaiar et al., "Life/Sci/Pharmacol. Lett.", 54:5–9, 1994.
Bourinbaiar et al., "Contraception", 49:131–137, Feb., 1994.
Dimitrov et al., "J. Virol.", 67:2182–2190, 1993.
Bourinbaiar, "Acta Virol.", 38:59–61, 1994.
Trinus, Pharmakoterapertichesky Spravocnik, 2nd edition, Zdorov'ia Publishers, yKiev, 1972, p. 362.

*Primary Examiner*—Jerome D. Goldberg
*Attorney, Agent, or Firm*—Abelman, Frayne & Schwab

[57] ABSTRACT

The invention relates to the use of gramicidin as an active ingredient of a spermicide with virucidal activity against human immunodeficiency virus (HIV)—a causative agent of a sexually transmitted disease—AIDS.

4 Claims, 1 Drawing Sheet

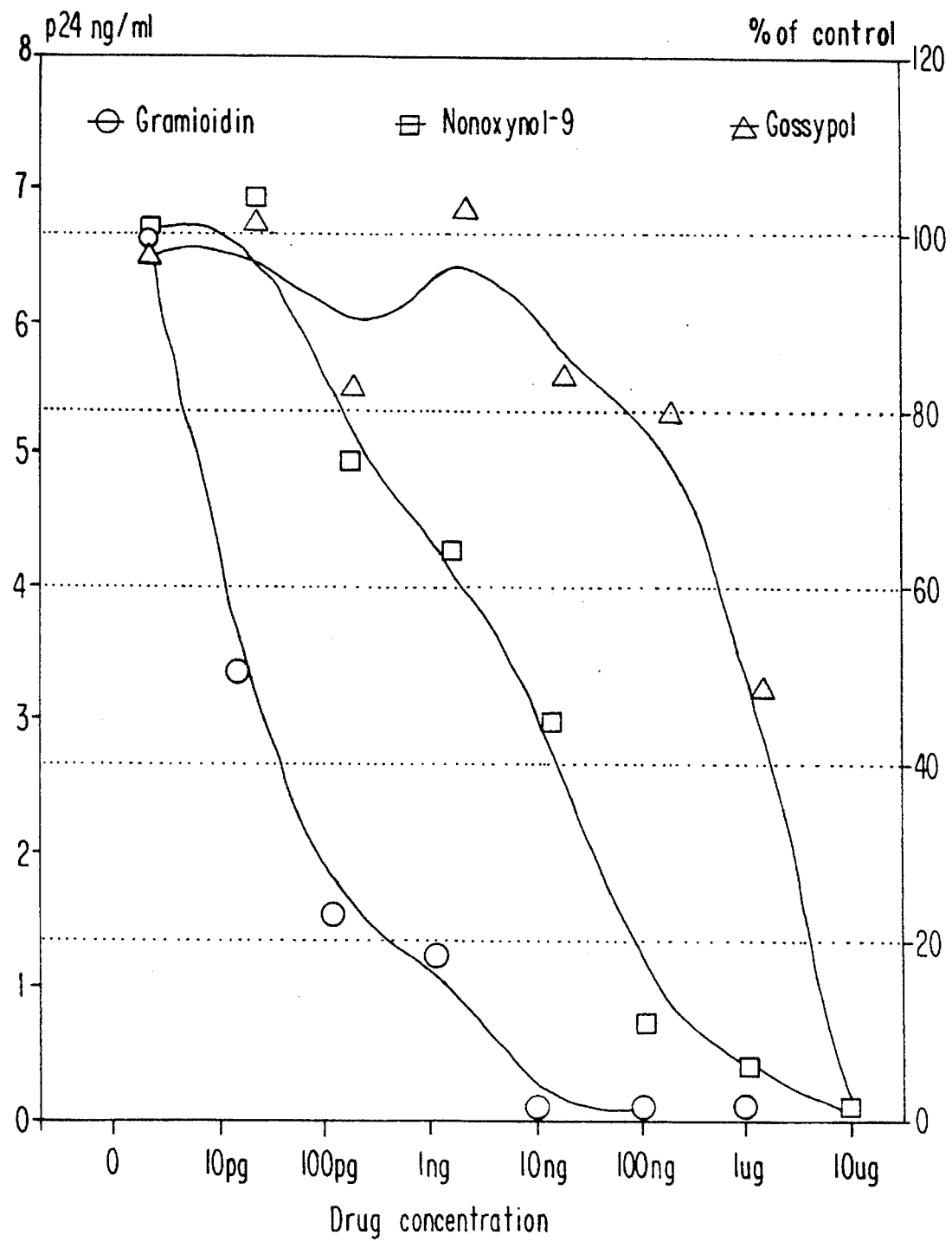

GRAMICIDIN AS A SPERMICIDE AGAINST SEXUAL TRANSMISSION OF HIV

FIELD OF THE INVENTION

The present invention relates to the field of preventing vital infections and, in particular, is directed to a method of preventing retroviral infections. More specifically, this invention relates to a method of preventing or inhibiting the sexual transmission of retroviral infections by employing gramicidin as the active ingredient in a spermicide and, therefore, gramicidin as such, and its chemical synthesis are not a part of the present invention.

BACKGROUND OF THE INVENTION

A group of viruses known as retroviruses are of particular concern because they cause diseases that are potentially lethal to an infected host. Retroviruses are a subgroup of RNA viruses that replicate by a reverse transcription mechanism using DNA polymerase that converts viral RNA into proviral DNA which becomes a part of the host cell DNA.

At the present time, several retroviruses are recognized as causative agents of infections in humans. For example, human T cell lymphotropic viruses of type 1 and 2 (HTLV-1 and HTLV-2) are known as the causative agents of T cell leukemia and debilitating neurological diseases. Human immunodeficiency virus (HIV-1 and HIV-2) has been recognized as the causative agent of acquired immunodeficiency syndrome (AIDS) and AIDS-related complex (ARC).

HIV can be found in genital secretions, e.g., semen or vaginal fluid, and can be transmitted during sexual intercourse. Thus, AIDS is regarded as a venereal disease with a fatal outcome, and in as many as 80% of the world's cases is caused by the passage of HIV across the genital mucosa. The prevention of the sexual transmission of HIV is an issue of fundamental and paramount importance that needs to be addressed and resolved. Recent clinical surveys have agreed that currently used spermicides with known antiviral activity, e.g., nonoxynol-9, will not satisfactorily restrict the spread of HIV. (Cates et al. *Family Planning Perspective*, 24:75–84, 1992). Therefore, improved contraceptive agents with virucidal activity are urgently in need of identification, since the majority of the world's AIDS cases are contracted through heterosexual contact. (Merson, *Science*, 260: 1266–8, 1993).

Gramicidin, which is a cation channel forming ionophore with antibacterial properties, was isolated from a strain of soil bacteria *Bacillus brevis* by Rene Dubos, a French scientist at the Rockefeller University. Following his initial recovery of a linear pentadecapeptide form in 1941, Soviet scientists reported a cyclic form of gramicidin designated as S. These peptides are remarkably stable natural substances and can retain their biological activity after exposure to extreme variations of temperature. For example, gramicidin S retains its biological activity even after 30 minutes in an autoclave.

Gramicidin is an over-the-counter spermicide routinely used in the former Soviet Union (FSU) as an active component of contraceptive gels and suppositories (Kashkin et al., *Antibiotiky*, 347–355, 1970). When it is available, millions of units of it are sold in the FSU every year. In Western countries, gramicidin has never been considered or used for spermicidal use. In the United States, gramicidin is used exclusively in topical ophthalmic preparations (Neosporin) in combination with other antibiotics, such as neomycin and polymyxin B with a concentration of less than 0.025% or 25 µg/ml rarely causing irritation as it is poorly absorbed by the skin or mucous membranes. This is probably due to the fact that gramicidin is freely soluble in ethanol, but insoluble in water, acids, and alkalies. In addition to antibacterial activity, gramicidin also exhibits activity against fungal (e.g., *Candida albicans*), bacterial (gonorrhea) and protozoan (chlamydia) growth. These properties will greatly enhance the potential of gramicidin against conventional sexually transmitted diseases (STDs).

The present inventor has discovered and reported that gramicidin displays useful anti-HIV activity in vitro (Boubinbaiar et al., *Life/Sci/Pharmacol. Lett.* 54:5–9, 1994) and also can be useful in vivo in the treatment of HIV infection. There are no known reports in the scientific literature demonstrating specifically the direct anti-viral effects of gramicidin, whether in its linear or cyclic forms.

Accordingly, it is a primary object of the present invention to provide a method to prevent the transmission of HIV in vitro.

It is also an object of the present invention to provide a method to prevent the transmission of HIV in vivo during sexual intercourse.

These and other objects of the invention will become apparent from the specification which follows hereafter.

SUMMARY OF THE INVENTION

The invention comprises a method for preventing or inhibiting the transmission of HIV in vitro, as well as preventing or inhibiting the transmission of HIV infection in vivo.

More specifically, the invention comprises a method for preventing the transmission of HIV infection by employing a therapeutically effective dose of gramicidin, as the active component of a spermicide upon sexual intercourse.

The method is based upon employing either linear gramicidin, or gramicidin S, or a mixture thereof, as a spermicide during heterosexual or homosexual intercourse in an amount and for a period of time both of which are sufficient to exert a protective effect against the sexual transmission of HIV.

BRIEF DESCRIPTION OF THE DRAWINGS

The drawing shows the anti-HIV effect of gramicidin in comparison with two unrelated spermicides, namely, nonoxynol-9 and gossypol.

DETAILED DESCRIPTION OF THE INVENTION

Preventing or inhibiting the transmission of HIV during sexual intercourse is achieved by employing a linear or cyclic gramicidin, or a mixture thereof, as the active component of a spermicide a variety of delivery vehicles e.g., a gel, a foam or a suppository, etc., at concentrations of from about 0.02 mg/dose to about 2.0 g/dose. The dosage of gramicidin should be sufficient to reach a local concentration in the vagina or the rectum of not less than 10 ng.

It has been observed experimentally that from 10 pg to about 10 ng of gramicidin can achieve 50% ($IC_{50}$) and 100% ($IC_{100}$) inhibition, respectively, of HIV without any evidence of attendant cytotoxicity.

It has also been determined that when gramicidin is compared to the presently used commercial spermicide nonoxynol-9, and the male anti-fertility agent gossypol, the $IC_{50}$ and $IC_{100}$ value were significantly higher, indicating that these compounds were not nearly as effective as gramicidin in inhibiting or preventing the transmission of HIV infection. (Bourinbaiar et al., *Contraception*, 49:131–137, February, 1994.) While complete protection against HIV infection was provided by nonoxynol-9 and gossypol when administered in a 10 μg/ml dose, the concentration was three orders of magnitude greater than that needed to achieve $IC_{100}$ for gramicidin. This is shown in FIG. 1, which will be discussed hereinafter.

Thus, it can readily be seen that the effective antiviral concentration of gramicidin required for complete HIV inactivation is a 1000-fold lower than the dosage needed for nonoxynol-9 or gossypol, which are established contraceptive agents.

The gramicidin of the present invention may be derived from chemical or enzymatic synthesis or may be a recombinant polypeptide which has been engineered genetically in accordance with genetic engineering principles well-known in the art.

The invention also contemplates in another embodiment the administration of a combination of spermicides which exhibit anti-HIV activity. For example, nonoxynol-9 and benzalkonium chloride, chlorhexidine, or dextran sulfate can be combined with gramicidin.

The anti-HIV action of gramicidin was demonstrated by testing particular compounds in vitro against de novo infection of MT-4 lymphocytes by HIV. The following test procedure was employed.

EXAMPLE

In a classical virology assay aimed at testing the antiviral activity of a drug, the virus is added in the presence of a drug to target cells for the determined period of inoculation time, e.g., 1 hour, and then nonadsorbed virus is washed away and inoculated cells are exposed again to a fresh drug. After several days, a period corresponding to the replication cycle of the virus, the dose-effect of the drug is tested by measuring the quantity of newly-synthesized virus in the culture supernates of inoculated cells. But this strategy is not truly representative of the in vivo situation. It is clear that in a real-life situation the virus is not "flushed" from a human body prior to drug administration. Rather, the "mixture" of the pathogen, drug and target cells or tissues ought to be present in a continuous manner in a human body until the drug is no more active. In the present assay, virus, drug and cells were left without washing in the culture until tested for virus production 3 days later. This period of time presents one full cycle of HIV replication, Dimitrov et al., *J. Virol.* 67:2182–90, 1993. It is believed that this type of approach represents more closely and simulates the situation which exists in vivo.

A commercial preparation of gramicidin purchased from Sigma (St. Louis, Mo.) and comprises a mixture of the three gramicidins: A, B, and C, constituting 80, 6, 14 percent respectively. Each gramicidin consists of 2 subspecies, one with valine in position 1, comprising 80–95% of the component, and the other with isoleucine in position 1. The drug was prepared as a stock concentration of 1 mg/ml in 70% ethanol.

Antiviral assay. To determine whether gramicidin may affect HIV infectivity of MT-4 T lymphocytes ($10^5$ cells/ml) were inoculated with $10^7$ virions/ml of IIIB strain of HIV titrated on the basis of molecular weight of virion in relation to p24 concentration and the ratio of defective to infectious particles. (Bourinbaiar, *Acta Virol.*, Vol. 38, pg. 59–61 (1994.) Infection assay was carried out in 96-well culture plates containing serial ten-fold dilutions of gramicidin ranging from 10 μg/ml to 10 pg/ml. The MT-4 cells were cultured in the mixture of drug and viral inocula for 3 days in 200 μl RMPMI 1640/10% FCS until tested for virus production. The amount of original viral inoculum left for 3 days in 200 μl volume of medium without lymphocytes has been subtracted from the experimental values.

p24 ELISA. Reduction of productive infection was evaluated by a commercial ELISA kit for viral core gag p24 product according to the manufacturer's instructions (Coulter, Hialeah, Fla.) as follows. Detergent-lysed samples of viral culture medium that were incubated in wells (96-well format), precoated with anti-p24 antibody, were screened for gag antigen by adding biotin-labeled anti-p24 antibody followed by streptavidin-peroxidase conjugate. The amount of captured p24 was measured by comparing the optical density (450 nm) of peroxidase substrate with supplied standards containing known amounts of p24. The lower limit of reliable sensitivity of this kit is 7.8 pg/ml.

Cytotoxicity assay. The toxicity of gramicidin after three (3) days of continuous exposure was evaluated by two methods carried out simultaneously in the same wells: [$^3$H] thymidine uptake and colorimetric tetrazolium salt (XTT; Sigma) assay that estimates the activity of mitochondrial hydrogenases converting XTT into formazan dye.

Based on five (5) separate experiments with three (3) replicates for each dilution of gramicidin, it can be concluded that 50% and 100% ($IC_{50}$ and $IC_{100}$) inhibition of HIV infection was achieved by 10 pg and 10 ng of gramicidin, respectively (See FIG. 1). The $IC_{50}$ and $IC_{100}$ values for nonoxynol-9 and gossypol were higher, implying that these compounds were not as efficient as gramicidin. Complete protection against HIV infection provided by nonoxynol-9 and gossypol was achieved by 10 μg/ml dose. This concentration is three orders of magnitude higher than $IC_{100}$ of gramicidin as shown in Table 1 below.

TABLE 1

| Approximate $\log_{10}$ inhibitory concentrations (IC) of spermicides in relation to the cytotoxicity (CC) | | | | |
|---|---|---|---|---|
| Drug | $IC_{50}$ | $IC_{100}$ | $CC_{100}$ | TI* |
| Gramicidin | 10 pg | 10 ng | 10 μg | 1000 |
| Nonoxynol-9 | 10 ng | 10 μg | 10 μg | 1 |
| Gossypol | 1 μg | 10 μg | 10 μg | 1 |

*TI is the therapeutic index and was determined as the ratio between $CC_{100}$ and $IC_{100}$ concentrations of drugs. Higher values of TI are indicative of better selectivity.

In addition, a set of experiments were carried out using two primary HIV-1 isolates. The results were the same as with the laboratory strain of HIV. The $IC_{50}$ and $IC_{100}$ doses required to inhibit de novo HIV infection were similar to the IIIB strain. The toxicity against PBMC was within the same range as with MT-4 lymphycotes. Obtained values agree well with the figures reported in the literature. A recent review of in vitro investigations with nonoxynol-9 indicated that the protective effect was generally observed at 0.05% or 50 μg/ml dose. A similar figure can be deduced from in vitro studies dealing with the male antifertility agent, gossypol, that has been reported to abrogate HIV infection at 100 μM concentration or an equivalent of 50 μg/ml.

Gramicidin is known to affect cation conductivity across the plasma membrane and miscibility behavior of lipid mixtures organized as binary structures. Incidentally, there is good evidence that the infectious capacity of HIV depends on the membrane fluidity of target cells and impaired permeability for cations. Emergence of syncytial cells resulting from fusion of the viral envelope with the membrane of target cells is commonly associated with productive HIV infection. A good correlation has been found between the reduction in p24 production and the decline in the number of giant syncytial cells in gramicidin-treated wells. No signs of cytophatic effect were observed, e.g., "membrane ballooning" and syncytia in wells where the viral replication was completely inhibited. This suggests that, indeed, a relationship exists between inhibition of virus-induced fusion and the antiviral effect of gramicidin. However, alternative mechanisms of gramicidin action cannot be excluded, such as the down-regulation of proviral genome transcription.

What is claimed is:

1. A method for the prevention of sexual transmission of HIV in a human host in need thereof, said method comprising administering by topical application in the vagina or rectum of the human host in need thereof a quantity of gramicidin which is sufficient to exert a protective effect.

2. A method as defined in claim 1, said method comprising administering from 0.02 mg to 2.0 mg of gramicidin per dose.

3. A method is defined in claim 1, which requires a sufficient amount of gramicidin to reach a local concentration in the vagina or the rectum of not less than 10 ng within a period of time sufficient to provide adequate preventive protection.

4. A method as defined in claim 1, said method comprising gramicidin as an active ingredient of a spermicide in a pharmaceutically suitable vehicle selected from the group consisting of gels, foams, and suppositories.

* * * * *